United States Patent
Souza et al.

(10) Patent No.: US 11,345,706 B2
(45) Date of Patent: May 31, 2022

(54) CRYSTALLINE FORMS OF ACALABRUTINIB

(71) Applicant: Apotex Inc., Toronto (CA)

(72) Inventors: Fabio E. S. Souza, Mississauga (CA); Bahareh Khalili, Mississauga (CA); Annyt Bhattacharyya, Hamilton (CA); Wancheng Guo, Tianjin (CN); Jingda Zhang, Tianjin (CN); Kun Cheng, Tianjin (CN); Kangying Li, Tianjin (CN)

(73) Assignee: Apotex Inc., Toronto (CA)

( * ) Notice: Subject to any disclaimer, the term of this patent is extended or adjusted under 35 U.S.C. 154(b) by 14 days.

(21) Appl. No.: 16/639,668

(22) PCT Filed: Aug. 23, 2018

(86) PCT No.: PCT/CA2018/051015
§ 371 (c)(1),
(2) Date: Feb. 17, 2020

(87) PCT Pub. No.: WO2019/041026
PCT Pub. Date: Mar. 7, 2019

(65) Prior Publication Data
US 2021/0130360 A1    May 6, 2021

Related U.S. Application Data

(60) Provisional application No. 62/551,418, filed on Aug. 29, 2017.

(51) Int. Cl.
*C07D 487/04* (2006.01)

(52) U.S. Cl.
CPC ........ *C07D 487/04* (2013.01); *C07B 2200/13* (2013.01)

(58) Field of Classification Search
None
See application file for complete search history.

(56) References Cited

U.S. PATENT DOCUMENTS 9,796,721 B2    10/2017    Blatter et al.
2017/0029428 A1*    2/2017    Blatter .................... A61P 19/00
2019/0382405 A1    12/2019    Sheng et al.

FOREIGN PATENT DOCUMENTS

WO    2017002095 A1    1/2017
WO    2018064797 A1    4/2018

OTHER PUBLICATIONS

Bernstein, Polymorphism in Molecular Crystals, 2002, pp. 9-10, Oxford University Press, New York, United States.
Ding et al., "Extended-Release and Targeted Drug Delivery Systems", Remington the Science and Practice of Pharmacy, 2006, pp. 939-964, 21st Edition, Lippincott Williams & Wilkins, Philadelphia, United States.
Porter, "Coating of Pharmaceutical Dosage Forms", Remington the Science and Practice of Pharmacy, 2006, pp. 929-938, 21st Edition, Lippincott Williams & Wilkins, Philadelphia, United States.
Rudnic et al., "Oral Solid Dosage Forms", Remington the Science and Practice of Pharmacy, 2006, pp. 889-928, 21st Edition, Lippincott Williams & Wilkins, Philadelphia, United States.

* cited by examiner

*Primary Examiner* — Clinton A Brooks
*Assistant Examiner* — Jennifer C Sawyer
(74) *Attorney, Agent, or Firm* — The Webb Law Firm (57) ABSTRACT

The present invention provides crystalline forms of Acalabrutinib, Specific crystalline forms provided by the present invention include Acalabrutinib Form APO-I, a co-crystal of Acalabrutinib and urea; APO-II, a co-crystal of Acalabrutinib and nicotinamide; APO-III, a co-crystal of Acalabrutinib and L-sorbitol; APO-IV, a crystalline form of Acalabrutinib; and APO-V, a co-crystal of Acalabrutinib and urea.

9 Claims, 5 Drawing Sheets

CRYSTALLINE FORMS OF ACALABRUTINIB

CROSS-REFERENCE TO RELATED APPLICATIONS

This application is the United States national phase of International Application No. PCT/CA2018/051015 filed Aug. 23, 2018, and claims priority to U.S. Provisional Patent Application No. 62/551,418 filed Aug. 29, 2017, the disclosures of which are hereby incorporated by reference in their entirety.

TECHNICAL FIELD

The present invention is directed to crystalline forms of Acalabrutinib, processes for the preparation thereof, pharmaceutical compositions containing these forms, and their use in the treatment of Bruton's tyrosine kinase (Btk) mediated disorders, including certain forms of cancer.

BACKGROUND

Acalabrutinib (1), or 4-{8-amino-3-[(2S)-1-(but-2-ynoyl) pyrrolidin-2-yl]imidazo[1,5-a]pyrazin-1-yl}-N-(pyridin-2-yl)benzamide, exhibits activity as a Bruton's tyrosine kinase inhibitor, and is the active ingredient in CALQUENCE®, which is indicated for the treatment of adult patients with mantle cell lymphoma (MCL) who have received at least one prior therapy.

(1)

U.S. Pat. No. 9,796,721 B2 and WO 2017/002095 A1 disclose salts and crystalline forms, including hydrates and solvates of Acalabrutinib. Form I is described as an anhydrous non-solvated form and Form II as a variable trihydrate form. Form I and Form II are stated to be subject to interconversion, which is dependent on the water activity level in the solvents used for their preparation. Further forms III-VIII, which are characterized as hydrated, anhydrous or solvated forms, are classified as being metastable. U.S. Pat. No. 9,796,721 further discloses co-crystal forms of Acalabrutinib with L-proline, L-arabitol, D-sorbitol and succinic acid are also described.

The crystalline forms reported in U.S. Pat. No. 9,796,721 B2 and WO 2017/002095 A1 are associated with various problems, including relative instability and tendencies for interconversion under various levels of humidity conditions; the incorporation of toxic or odorous solvents; reproducibility problems associated with the variable incorporation of water into the hydrated forms; and preparations requiring manufacturing steps, such as heating and dehydrating solids at temperatures as high as 100° C. that are undesired in commercial processes. The tendency of forms to interconvert at various levels of humidity limits their usefulness in commercial products since it can require specialised practices to avoid interconversion during handling, storage and formulation activities. Furthermore, the variable nature of these forms has regulatory implications, as the characteristics of an active pharmaceutical ingredient must be well-defined and controlled.

U.S. Pat. No. 9,796,721 B2 reports that Acalabrutinib is a weakly acidic drug which exhibits a pH-dependent solubility, having solubility at the low pH of the stomach, but being practically insoluble at pH values of greater than 4. This differential solubility is reported to be problematic upon administration of Acalabrutinib to patient taking an acid-reducing agent, such as a proton-pump inhibitor, which can alter the pH of the stomach to values above 4, and lead to a reduction in Acalabrutinib exposure. Since co-administration of a gastric acid reducing agent is common during cancer treatment to address the gastric irritation which can accompanies such treatment, the differential solubility of Acalabrutinib is a significant concern for these patients since it can affect the efficacy of their treatment. Methods that are reported in U.S. Pat. No. 9,796,721 B2 to overcome the effect of acid-reducing agents on absorption of Acalabrutinib include adjusting the drug formulation by, for example, adding an acidulant to increase acidity around the drug substance or by adding an excipient to prolong the exposure of the drug substance to the acidic environment of the stomach, such as a polymer.

Different crystalline forms of the same compound may have different packing, thermodynamic, spectroscopic, kinetic, surface and mechanical properties. For example, different crystalline forms may have different stability properties. A particular crystalline form may be more sensitive to heat, relative humidity (RH) and/or light. Alternatively or additionally, a particular crystalline form may provide more compressibility and/or density properties thereby providing more desirable characteristics for formulation and/or product manufacturing. Particular crystalline forms may also have different dissolution rates, thereby providing different pharmacokinetic parameters, which allow for specific forms to be used in order to achieve specific pharmacokinetic targets. Additionally, the particular solubility characteristics of a given crystalline form in relation to undesired impurities can result in differences in the chemical purity of different crystalline forms upon isolation. Differences in stability may result from changes in chemical reactivity, such as differential oxidation. Such properties may provide for more suitable product qualities, such as a dosage form that is more resistant to discolouration when comprised of a specific crystalline form. Different physical properties of crystalline forms may also affect their processing. For example, a particular crystalline form may be more resistant to flow, or may be more difficult to filter and/or wash.

Although general approaches to crystalline form screening of active pharmaceutical ingredients are known, it is well established that the prediction of whether any given compound will exhibit polymorphism is not possible. Furthermore, prediction of the properties of any unknown crystalline forms, and how they will differ from other crystalline forms of the same compound, remains even more elusive (Joel Bernstein, *Polymorphism in Molecular Crystals*, Oxford University Press, New York, 2002, page 9).

Therefore, there exists a need for novel crystalline forms of Acalabrutinib for use in providing improved drug products containing Acalabrutinib and their manufacture.

SUMMARY

The present invention provides Acalabrutinib crystalline forms, and in particular, multiple-component crystalline forms comprising Acalabrutinib and a co-former selected from urea, nicotinamide and L-sorbitol, each co-former having an established safety record. Owing to the use of co-formers with an established safety record, it is expected that the Acalabrutinib crystalline forms of the present invention can safely be used in materials intended for use in the preparation of pharmaceutical compositions intended for administration to humans or animals. Further, each of the co-formers is a highly water soluble compound, with urea and nicotinamide also known as hydrotropic agents that have been used for the solubilisation of poorly water soluble compounds, including drug substances. Thus, the provision of crystalline forms of Acalabrutinib comprising these highly water-soluble components is expected to provide improvements in the solubility of Acalabrutinib.

The Acalabrutinib crystalline forms of the present invention can also be prepared by efficient and industrially compatible processes. This is in contrast with the high-throughput screening results reported in U.S. Pat. No. 9,796,721 B2, which showed that attempts at co-crystallization of Acalabrutinib with nicotinamide afforded amorphous material, while co-crystallization of Acalabrutinib with urea could not be scaled up successfully.

Additionally, embodiments of the present invention exhibit form stability at high temperature and high humidity, which provides benefits in terms of their handling, storage and use in formulation.

Accordingly, in a first aspect of the present invention, there is provided a crystalline form of Acalabrutinib that is a co-crystal of Acalabrutinib and urea. Preferably, in the co-crystal of the first aspect, the molar ratio of Acalabrutinib to urea is between approximately 1:0.5 and 1:3. More preferably, the molar ratio of Acalabrutinib to urea is between approximately 1:1 and 1:3. Even more preferably, the molar ratio of Acalabrutinib to urea is between approximately 1:1.5 and 1:2.5. Most preferably, the molar ratio of Acalabrutinib to urea is approximately 1:2.

In a second aspect of the present invention, there is provided a crystalline form of Acalabrutinib, APO-I, that is a co-crystal of Acalabrutinib and urea characterized by a powder X-ray diffraction (PXRD) diffractogram comprising peaks, expressed in degrees 2θ (±0.2°), at 5.4°, 7.3° and 10.0°. In a preferred embodiment of the second aspect, the PXRD diffractogram further comprises at least three peaks, expressed in degrees 2θ (±0.2°), selected from the group consisting of: 10.4°, 11.4°, 11.8°, 12.8°, 15.3°, 17.0°, 18.4°, 20.1°, 20.8° and 21.3°. In another preferred embodiment of the second aspect, the PXRD diffractogram further comprises peaks, expressed in degrees 2θ (±0.2°), at 10.4°, 11.4°, 11.8°, 12.8°, 15.3°, 17.0°, 18.4°, 20.1°, 20.8° and 21.3°. In this second aspect of the invention, the molar ratio of Acalabrutinib to urea is preferably between approximately 1:1 and 1:3. More preferably, the molar ratio of Acalabrutinib to urea is between approximately 1:1.5 and 1:2.5. Most preferably, the molar ratio of Acalabrutinib to urea is approximately 1:2.

In a third aspect of the present invention, there is provided a crystalline form of Acalabrutinib that is a co-crystal of Acalabrutinib and nicotinamide. Preferably, in the co-crystal of the third aspect, the molar ratio of Acalabrutinib to nicotinamide is between approximately 1:0.5 and 1:3. More preferably, the molar ratio of Acalabrutinib to nicotinamide is between approximately 1:1 and 1:3. Even more preferably, the molar ratio of Acalabrutinib to nicotinamide is between approximately 1:1.5 and 1:2.5. Most preferably, the molar ratio of Acalabrutinib to nicotinamide is approximately 1:2.

In a fourth aspect of the present invention, there is provided a crystalline form of Acalabrutinib, APO-II, that is a co-crystal of Acalabrutinib and nicotinamide characterized by a PXRD diffractogram comprising peaks, expressed in degrees 2θ (±0.2°), at 5.8°, 7.2° and 14.6°. In a preferred embodiment of the fourth aspect, the PXRD diffractogram further comprises at least three peaks, expressed in degrees 2θ (±0.2°), selected from the group consisting of: 9.2°, 10.2°, 11.4°, 12.8°, 16.0°, 18.5°, 21.1°, 21.9°, 23.4° and 24.1°. In another preferred embodiment of the fourth aspect, the PXRD diffractogram further comprises peaks, expressed in degrees 2θ (±0.2°), at 9.2°, 10.2°, 11.4°, 12.8°, 16.0°, 18.5°, 21.1°, 21.9°, 23.4° and 24.1°. In this fourth aspect of the invention, the molar ratio of Acalabrutinib to nicotinamide is preferably between approximately 1:1 and 1:3. More preferably, the molar ratio of Acalabrutinib to nicotinamide is between approximately 1:1.5 and 1:2.5. More preferably, the molar ratio of Acalabrutinib to nicotinamide is approximately 1:2.

In a fifth aspect of the present invention, there is provided a crystalline form of Acalabrutinib that is a co-crystal of Acalabrutinib and L-sorbitol. Preferably, in the co-crystal of the fifth aspect, the molar ratio of Acalabrutinib to L-sorbitol is between approximately 1:0.5 and 1:2.5. More preferably, the molar ratio of Acalabrutinib to L-sorbitol is between approximately 1:0.5 and 1:2. Even more preferably, the molar ratio of Acalabrutinib to L-sorbitol is between approximately 1:0.75 and 1:1.25. Most preferably, the molar ratio of Acalabrutinib to L-sorbitol is approximately 1:1.

In a sixth aspect of the present invention, there is provided a crystalline form of Acalabrutinib, APO-III, that is a co-crystal of Acalabrutinib and L-sorbitol characterized by a PXRD diffractogram comprising peaks, expressed in degrees 2θ (±0.2°), at 8.5°, 10.8° and 12.3°. In a preferred embodiment of the sixth aspect, the PXRD diffractogram further comprises at least three peaks, expressed in degrees 2θ (±0.2°), selected from the group consisting of: 11.6°, 12.8°, 13.4°, 14.1°, 16.2°, 17.8° and 20.3°. In another preferred embodiment of the sixth aspect, the PXRD diffractogram further comprises peaks, expressed in degrees 2θ (±0.2°), at 11.6°, 12.8°, 13.4°, 14.1°, 16.2°, 17.8° and 20.3°. In this sixth aspect of the invention, the molar ratio of Acalabrutinib to L-sorbitol is preferably between approximately 1:0.5 and 1:1.5. More preferably, the molar ratio of Acalabrutinib to L-sorbitol is approximately 1:1.

In a seventh aspect of the present invention, there is provided a crystalline form of Acalabrutinib, APO-IV, characterized by a PXRD diffractogram comprising peaks, expressed in degrees 2θ (±0.2°), at 7.5°, 10.9° and 12.6°. In a preferred embodiment of the seventh aspect, the PXRD diffractogram further comprises at least three peaks, expressed in degrees 2θ (±0.2°), selected from the group consisting of: 13.9°, 14.8°, 17.2°, 18.1°, 19.4°, 20.8°, 21.7°, 22.6° and 24.3°. In another preferred embodiment of the seventh aspect, the PXRD diffractogram further comprises peaks, expressed in degrees 2θ (±0.2°), at 13.9°, 14.8°, 17.2°, 18.1°, 19.4°, 20.8°, 21.7°, 22.6° and 24.3°.

In an eighth aspect of the present invention, there is provided a crystalline form of Acalabrutinib, APO-V, characterized by a PXRD diffractogram comprising peaks, expressed in degrees 2θ (±0.2°), at 5.4°, 6.6° and 11.0°. In a preferred embodiment of the eighth aspect, the PXRD diffractogram further comprises at least three peaks, expressed in degrees 2θ (±0.2°), selected from the group consisting of: 10.1°, 13.2°, 15.1°, 17.3°, 19.9°, 21.1° and 22.2°. In another preferred embodiment of the eighth aspect, the PXRD diffractogram further comprises peaks, expressed in degrees 2θ (±0.2°), at 10.1°, 13.2°, 15.1°, 17.3°, 19.9°, 21.1° and 22.2°. In this eighth aspect of the invention, the molar ratio of Acalabrutinib to urea is preferably between approximately 1:1 and 1:3. More preferably, the molar ratio of Acalabrutinib to urea is between approximately 1:1.5 and 1:2.5. More preferably, the molar ratio of Acalabrutinib to urea is approximately 1:2. In this eighth aspect of the invention, the co-crystal has a weight percentage of water of between approximately 2.0 wt % and approximately 4.0 wt %. More preferably, the weight percentage of water is between approximately 2.5% and approximately 3.5%. Most preferably, the weight percentage of water is approximately 3.0%.

In a ninth aspect of the present invention, there is provided a pharmaceutical composition comprising a crystalline form of Acalabrutinib according to any one of the first, second, third, fourth, fifth, sixth, seventh or eighth aspects of the invention, and one or more pharmaceutically acceptable excipients. Preferably, the pharmaceutical composition is a solid oral dosage form. Most preferably, the pharmaceutical composition is a capsule.

In a tenth aspect of the present invention, there is provided a use of a crystalline form of Acalabrutinib according to any one of the first, second, third, fourth, fifth, sixth, seventh or eighth aspects of the invention, or the pharmaceutical composition of the ninth aspect of the invention, in the treatment of a Btk-mediated disorder. In a preferred embodiment of the tenth aspect, the Btk-mediated disorder is lymphoma or leukemia. In a further preferred embodiment of the tenth aspect, the lymphoma is mantle cell lymphoma (MCL).

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention are described, by way of example only, with reference to the attached Figures.

DETAILED DESCRIPTION

The present invention provides Acalabrutinib crystalline forms, including multiple-component crystalline forms comprised of Acalabrutinib and a co-former having an established safety record selected from urea, nicotinamide and L-sorbitol. Importantly, with respect to the use of these crystalline forms in the preparation of pharmaceutical compositions, each of the co-formers urea, nicotinamide (niacinamide) and L-sorbitol is included in both the U.S. Food & Drug Administration's (FDA's) Everything Added to Food in the United States (EAFUS) list, and the Inactive Ingredient Database (IID). The EAFUS list contains ingredients added directly to food that the FDA has either approved as food additives, or has listed or affirmed as being GRAS (Generally Recognized As Safe). The IID list provides information on inactive ingredients present in FDA-approved drug products. Once an inactive ingredient has appeared in an approved drug product, the inactive ingredient is not considered new, and may require a less extensive review the next time it is included in a new drug product. As such, it is expected that these co-formers can safely be used in materials intended for use in the preparation of pharmaceutical compositions intended for administration to humans or animals.

Further, the multiple-component crystalline forms of the present invention incorporate highly water soluble components, including urea and nicotinamide, which are also known hydrotropic agents that have been used for the solubilisation of poorly water soluble compounds. Thus, the provision of crystalline forms of Acalabrutinib comprising these highly water soluble components is expected to provide improvements in the solubility of Acalabrutinib, which has been classified according to the Biopharmaceutics Classification System (BCS) as a poorly soluble drug.

The Acalabrutinib crystalline forms of the present invention exhibit differences in properties when compared to the known crystalline forms of Acalabrutinib. Depending on the specific crystalline form of the invention used, properties that differ between the invention and known crystalline forms of Acalabrutinib include the following: packing properties such as molar volume, density and hygroscopicity; thermodynamic properties such as melting and solubility; kinetic properties such as dissolution rate and chemical/polymorphic stability; surface properties such as crystal habit; and/or mechanical properties such as hardness, tensile strength, compactibility, tableting, handling, flow, and blending.

Furthermore, the Acalabrutinib crystalline forms of the present invention exhibit stability under conditions of high temperature and high humidity. As reported in U.S. Pat. No. 9,796,721 B2, a number of solvated and hydrated forms of Acalabrutinib are metastable, undergoing dehydration/desolvation and/or form conversion depending on factors such as atmospheric humidity. This behavior introduces risk into the handling, storage and formulation of the drug substance, wherein specialized packaging and formulation alterations may be necessary to ensure quality and consistency, which can add to the cost and complexity of manufacturing the commercial drug product. In contrast, the present invention provides crystalline forms of Acalabrutinib which were unchanged following open exposure to conditions of 40° C./75% RH for at least 2 weeks.

Further, the Acalabrutinib crystalline forms of the present invention can be prepared by efficient and industrially compatible processes. These results are surprising and in contrast with the high-throughput screening results reported in U.S. Pat. No. 9,796,721 B2, which showed that attempts at the co-crystallization of Acalabrutinib with nicotinamide afforded amorphous material, while co-crystallization of Acalabrutinib with urea was not scalable.

Depending on the manner in which the embodiments of the invention are prepared, the methodology and instrument used for PXRD analysis, and the scale selected to display results, the intensity of a given peak observed in the PXRD diffractogram may vary when compared to the same peak in the representative PXRD diffractograms provided in FIGS. 1 to 5 to illustrate the embodiments of the invention provided herein. Thus, differences in relative peak intensities between peaks in a PXRD diffractogram for a given crystalline form may be observed when compared to the relative peak intensities of the peaks in the representative PXRD diffractograms of FIGS. 1 to 5. Any such differences may be due, in part, to the preferred orientation of the sample and its deviation from the ideal random sample orientation, the preparation of the sample for analysis, and the methodology applied for the analysis. Such variations are known and understood by a person of skill in the art, and any such variations do not depart from the invention disclosed herein.

In addition to the differences in relative peak intensities that may be observed in comparison to the representative PXRD diffractograms provided in FIGS. 1 to 5, it is understood that individual peak positions may vary between ±0.2° 2θ from the values observed in the representative PXRD diffractograms provided in FIGS. 1 to 5 for the crystalline forms of the invention, or listed in Tables 1 to 5. Such variations are known and understood by a person of skill in the art, and any such variations do not depart from the invention disclosed herein.

Further, it is understood that, depending on the instrument used for X-ray analysis and its calibration, uniform offsets in the peak position of each peak in a PXRD diffractogram of greater that 0.2° 2θ may be observed when compared to the representative PXRD diffractograms provided in FIGS. 1 to 5. Thus, PXRD diffractograms of the crystalline forms of the present invention may, in some circumstances, display the same relative peak positions as observed in the representative PXRD diffractograms provided in FIGS. 1 to 5, with the exception that each peak is offset in the same direction, and by approximately the same amount, such that the overall PXRD diffractogram is substantially the same in appearance as a PXRD diffractogram of FIGS. 1 to 5, with the exception of the uniform offset in peak positions. The observation of any such uniform peak shift in a PXRD diffractogram does not depart from the invention disclosed herein given that the relative peak positions of the individual peaks within the PXRD diffractogram remain consistent with the relative peak positions observed in the PXRD diffractograms of FIGS. 1 to 5 for the crystalline forms of the invention.

As used herein, the term 'crystalline form' refers to a substance with a particular arrangement of molecular components in its crystal lattice, and which may be identified by physical characterization methods such as PXRD. As used herein, the term crystalline form is intended to include single-component and multiple-component crystalline forms of Acalabrutinib. Single-component forms of Acalabrutinib consist solely of Acalabrutinib in the repeating unit of the crystal lattice. Multiple-component forms of Acalabrutinib include co-crystals, salts and solvates of Acalabrutinib wherein a co-former, counterion or solvent is also incorporated into the crystal lattice.

As used herein, the term 'co-crystal' refers to a multiple-component crystalline form containing both Acalabrutinib and a co-former that is solid under ambient conditions.

Multi-component crystalline forms comprising more than one type of molecule, such as co-crystals, may have some variability in the exact molar ratio of their components depending on a variety of conditions used. For example, a molar ratio of components within a multi-component crystalline form provides a person of skill in the art information as to the general relative quantities of the components of the crystalline form. In many cases, the molar ratio may vary by ±20% from a stated range. For example, with respect to the present invention, a molar ratio of 1:0.5 should be understood to include the ratios 1:0.4 and 1:0.6, as well as all of the individual ratios in between.

As used herein, the term "room temperature" refers to a temperature in the range of 20° C. to 25° C.

Unless defined otherwise herein, the term "approximately", when used in reference to molar ratios, allows for a variance of plus or minus 10%.

As used herein, when referring to water content, the term "weight percentage" (wt %) refers to the ratio: weight water in sample/(weight sample), expressed as a percentage.

When describing the embodiments of the present invention there may be a common variance to a given temperature or time that would be understood or expected by the person skilled in the art to provide substantially the same result. For example, when reference is made to a particular temperature, it is to be understood by the person skilled in the art that there is an allowable variance of ±5° C. associated with that temperature. When reference is made to a particular time, it is to be understood that there is an allowable variance of ±10 minutes when the time is one or two hours, and ±1 hour when longer periods of time are referenced.

In one embodiment of the present invention, there is provided a new crystalline form of Acalabrutinib, Acalabrutinib Form APO-I, which is a co-crystal of Acalabrutinib and urea. Preferably, in Acalabrutinib Form APO-I, the molar ratio of Acalabrutinib to urea is approximately 1:2.

Acalabrutinib Form APO-I can be characterized by a PXRD diffractogram comprising, among other peaks, characteristic peaks, expressed in degrees 2θ (±0.2°), at 5.4°, 7.3° and 10.0°. Preferably, the PXRD diffractogram further comprises at least three peaks, expressed in degrees 2θ (±0.2°), selected from the group consisting of 10.4°, 11.4°, 11.8°, 12.8°, 15.3°, 17.0°, 18.4°, 20.1°, 20.8° and 21.3°. More preferably, the PXRD diffractogram further comprises peaks, expressed in degrees 2θ (±0.2°), at 10.4°, 11.4°, 11.8°, 12.8°, 15.3°, 17.0°, 18.4°, 20.1°, 20.8° and 21.3°. PXRD studies of capped and uncapped samples of Acalabrutinib Form APO-I have shown that this crystal form is stable following storage in stability chambers maintained at 27° C./60% RH and 40° C./75% RH for at least 12 days.

Figure 1:
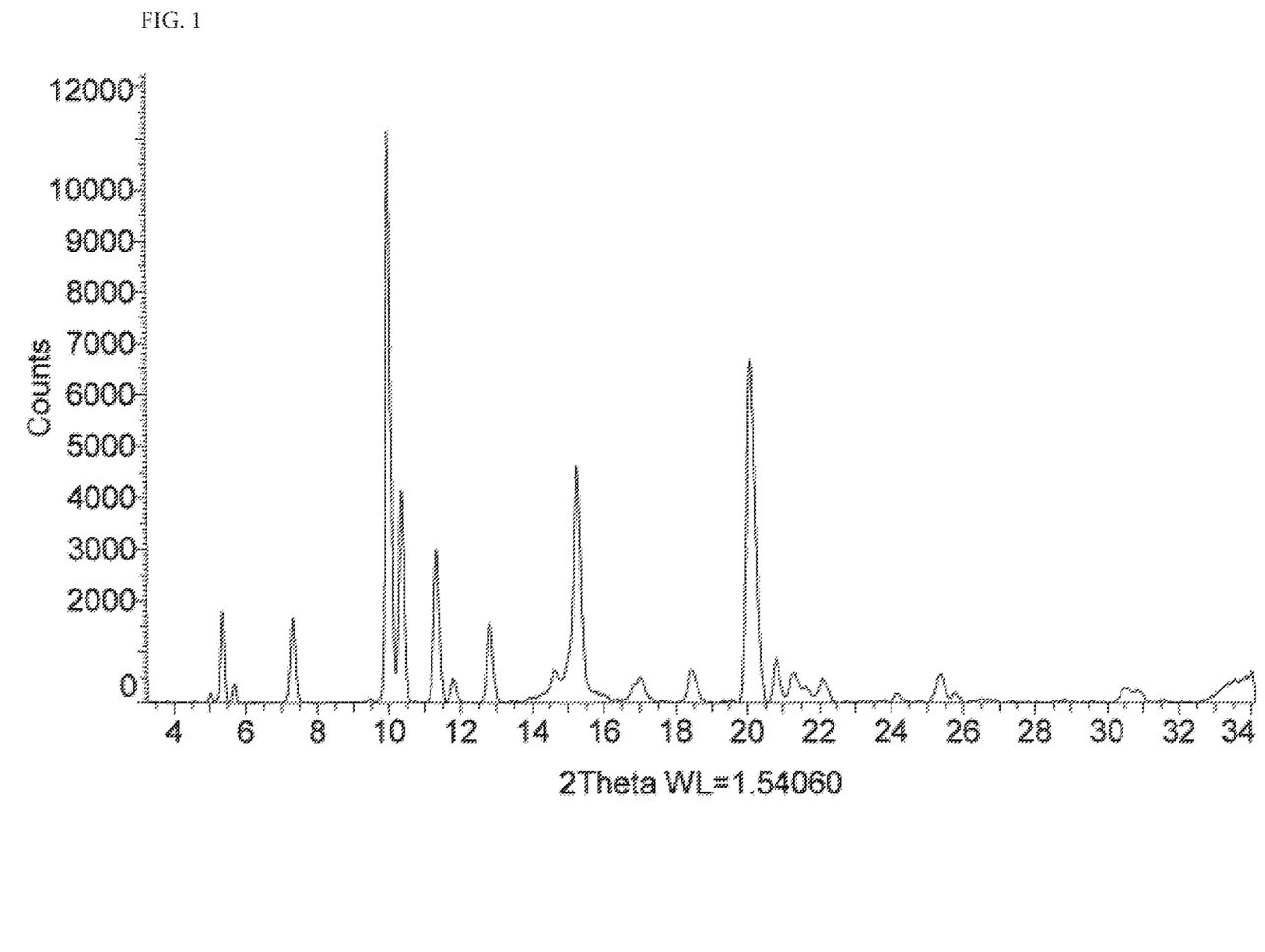
FIG. 1 is a representative PXRD diffractogram of Acalabrutinib Form APO-I as prepared in Example 2.

An illustrative PXRD diffractogram of Acalabrutinib Form APO-I, as prepared in Example 2, is shown in FIG. 1. A peak listing, comprising representative peaks from the PXRD diffractogram in FIG. 1, and their relative intensities, is provided in Table 1. Although illustrative of the PXRD diffractogram that is provided for the Acalabrutinib Form APO-I of the present invention, the relative intensities of the peaks are variable. Thus, depending on a particular sample, the prominence or relative intensity of the peaks observed may differ from those in the illustrative PXRD diffractogram and peak listing.

TABLE 1

Relative peak intensities of
Acalabrutinib Form APO-1 from FIG. 1

| Angle (°2θ) | Relative intensity (%) |
|---|---|
| 5.37 | 16.3 |
| 7.33 | 14.9 |
| 10.03 | 100.0 |
| 10.37 | 37.5 |
| 11.35 | 26.9 |
| 11.81 | 4.5 |
| 12.82 | 15.0 |

TABLE 1-continued

Relative peak intensities of
Acalabrutinib Form APO-1 from FIG. 1

| Angle (°2θ) | Relative intensity (%) |
|---|---|
| 15.27 | 47.6 |
| 17.04 | 8.9 |
| 18.44 | 7.1 |
| 20.11 | 60.7 |
| 20.82 | 9.6 |
| 21.32 | 7.2 |

A described in Examples 1 and 2, Acalabrutinib Form APO-I can be prepared by combining urea and Acalabrutinib in a solvent, preferably methanol, and maintaining the mixture at a suitable temperature, preferably in the range of room temperature to 60° C., followed by a period of cooling, if necessary. Alternatively, acetonitrile or acetone can be used as the solvent. The molar ratio of Acalabrutinib to urea is at least approximately 1:2, and is more preferably 1:4. Filtration of the resulting suspension provides Acalabrutinib Form APO-I having a PXRD diffractogram consistent with FIG. 1.

In a second embodiment of the present invention, there is provided a new crystalline form of Acalabrutinib, Acalabrutinib Form APO-II, which is a co-crystal of Acalabrutinib and nicotinamide. Preferably, in Acalabrutinib Form APO-II, the molar ratio of Acalabrutinib to nicotinamide is approximately 1:2.

Acalabrutinib Form APO-II can be characterized by a PXRD diffractogram comprising, among other peaks, characteristic peaks, expressed in degrees 2θ (±0.2°), at 5.8°, 7.2° and 14.6°. Preferably, the PXRD diffractogram further comprises at least three peaks, expressed in degrees 2θ (±0.2°), selected from the group consisting of 9.2°, 10.2°, 11.4°, 12.8°, 16.0°, 18.5°, 21.1°, 21.9°, 23.4° and 24.1°. More preferably, the PXRD diffractogram further comprises peaks, expressed in degrees 2θ (±0.2°), at 9.2°, 10.2°, 11.4°, 12.8°, 16.0°, 18.5°, 21.1°, 21.9°, 23.4° and 24.1°.

Figure 2:
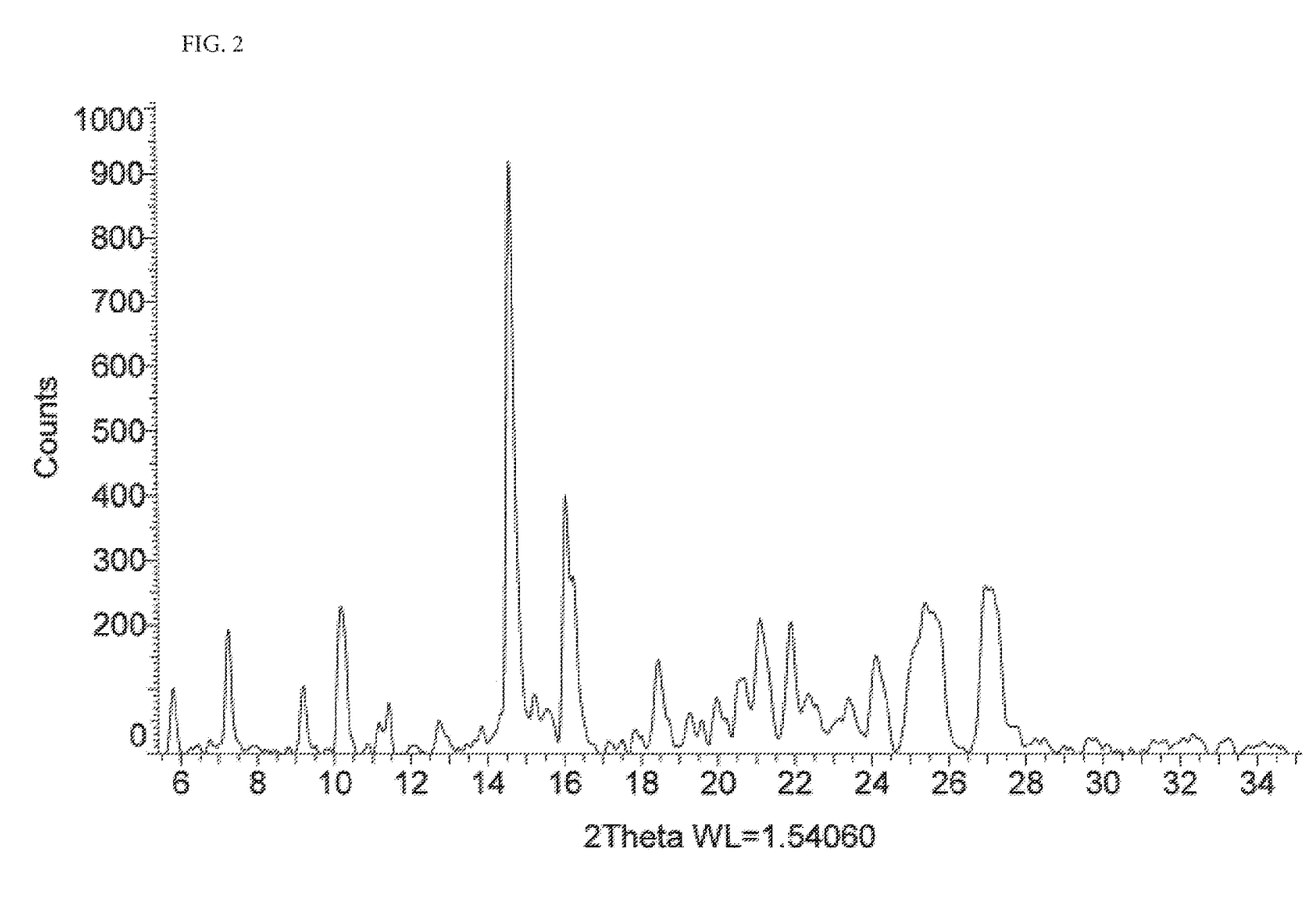
FIG. 2 is a representative PXRD diffractogram of Acalabrutinib Form APO-II as prepared in Example 3.

An illustrative PXRD diffractogram of Acalabrutinib Form APO-II, as prepared in Example 2, is shown in FIG. 2. A peak listing, comprising representative peaks from the PXRD diffractogram in FIG. 2, and their relative intensities, is provided in Table 2. Although illustrative of the PXRD diffractogram that is provided for the Acalabrutinib Form APO-II of the present invention, the relative intensities of the peaks are variable. Thus, depending on a particular sample, the prominence or relative intensity of the peaks observed may differ from those in the illustrative PXRD diffractogram and peak listing.

TABLE 2

Relative peak intensities of
Acalabrutinib Form APO-II from FIG. 2

| Angle (°2θ) | Relative intensity (%) |
|---|---|
| 5.80 | 7.2 |
| 7.24 | 17.9 |
| 9.20 | 8.7 |
| 10.20 | 17.4 |
| 11.42 | 6.0 |
| 12.78 | 4.6 |
| 14.59 | 100.0 |
| 16.02 | 43.0 |
| 16.24 | 29.6 |
| 18.47 | 11.9 |
| 19.99 | 6.2 |

TABLE 2-continued

Relative peak intensities of
Acalabrutinib Form APO-II from FIG. 2

| Angle (°2θ) | Relative intensity (%) |
|---|---|
| 20.65 | 9.9 |
| 21.13 | 20.3 |
| 21.90 | 18.1 |
| 23.43 | 7.3 |
| 24.12 | 15.0 |
| 25.59 | 23.3 |
| 27.04 | 26.9 |

As described in Example 3, Acalabrutinib Form APO-II can be prepared by combining nicotinamide and Acalabrutinib in a solvent, preferably acetone, and maintaining the mixture at a suitable temperature, preferably in the range of room temperature to 60° C., followed by a period of cooling, if necessary. Preferably, maintaining the mixture at a suitable temperature comprises subjecting the mixture to at least one cycle of the following temperature regime: heat from 20° C. to 50° C.; hold at 50° C. for 1 hour; cool from 50° C. to 20° C. in 10° C. intervals with a hold period of 1 hour at each interval (i.e., 40° C., 30° C., 20° C.). The molar ratio of Acalabrutinib to nicotinamide is at least approximately 1:2, and is more preferably 1:4. Filtration of the resulting suspension provides Acalabrutinib Form APO-II having a PXRD diffractogram consistent with FIG. 2.

In a third embodiment of the present invention, there is provided a new crystalline form of Acalabrutinib, Acalabrutinib Form APO-III, which is a co-crystal of Acalabrutinib and L-sorbitol. Preferably, in Acalabrutinib Form APO-III, the molar ratio of Acalabrutinib to L-sorbitol is approximately 1:1.

Acalabrutinib Form APO-III can be characterized by a PXRD diffractogram comprising, among other peaks, characteristic peaks, expressed in degrees 2θ (±0.2°), at 8.5°, 10.8° and 12.3°. Preferably, the PXRD diffractogram further comprises at least three peaks, expressed in degrees 2θ (±0.2°), selected from the group consisting of 11.6°, 12.8°, 13.4°, 14.1°, 16.2°, 17.8° and 20.3°. More preferably, the PXRD diffractogram further comprises peaks, expressed in degrees 2θ (±0.2°), at 11.6°, 12.8°, 13.4°, 14.1°, 16.2°, 17.8° and 20.3°.

Figure 3:
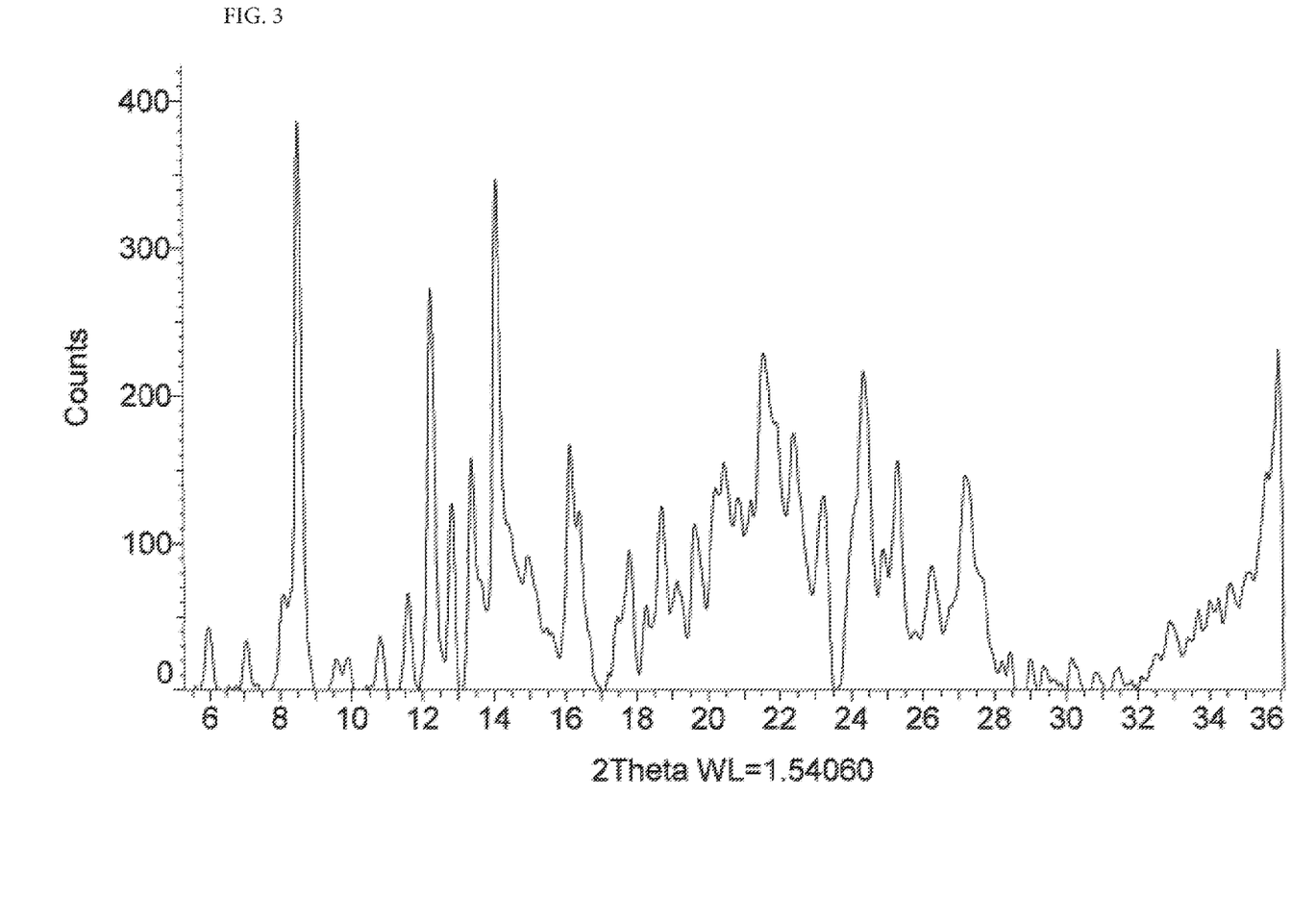
FIG. 3 is a representative PXRD diffractogram of Acalabrutinib Form APO-III as prepared in Example 4.

An illustrative PXRD diffractogram of Acalabrutinib Form APO-III, as prepared in Example 3, is shown in FIG. 3. A peak listing, comprising representative peaks from the PXRD diffractogram in FIG. 3, and their relative intensities, is provided in Table 3. Although illustrative of the PXRD diffractogram that is provided for the Acalabrutinib Form APO-III of the present invention, the relative intensities of the peaks are variable. Thus, depending on a particular sample, the prominence or relative intensity of the peaks observed may differ from those in the illustrative PXRD diffractogram and peak listing.

TABLE 3

Relative peak intensities of
Acalabrutinib Form APO-III from FIG. 3

| Angle (°2θ) | Relative intensity (%) |
|---|---|
| 7.08 | 9.4 |
| 8.06 | 26.3 |
| 8.53 | 75.5 |
| 10.79 | 14.7 |
| 11.59 | 19.2 |

TABLE 3-continued

Relative peak intensities of
Acalabrutinib Form APO-III from FIG. 3

| Angle (°2θ) | Relative intensity (%) |
|---|---|
| 12.26 | 100.0 |
| 12.76 | 36.8 |
| 13.41 | 30.3 |
| 14.08 | 99.4 |
| 16.21 | 30.5 |
| 17.76 | 33.6 |
| 20.27 | 46.3 |

As described in Example 4, Acalabrutinib Form APO-III can be prepared by combining L-sorbitol and Acalabrutinib in a solvent, preferably acetone, and maintaining the mixture at a suitable temperature, preferably in the range of room temperature to 60° C., followed by a period of cooling, if necessary. Preferably, maintaining the mixture at a suitable temperature comprises subjecting the mixture to at least one cycle of the following temperature regime: heat from 20° C. to 50° C.; hold at 50° C. for 1 hour; cool from 50° C. to 20° C. in 10° C. intervals with a hold period of 1 hour at each interval (i.e., 40° C., 30° C., 20° C.). The molar ratio of Acalabrutinib to L-sorbitol is at least approximately 1:1, and is more preferably 1:4. Filtration of the resulting suspension provides Acalabrutinib Form APO-III having a PXRD diffractogram consistent with FIG. 3.

In a fourth embodiment of the present invention, there is provided a new crystalline form of Acalabrutinib, Acalabrutinib Form APO-IV.

Acalabrutinib Form APO-IV can be characterized by a PXRD diffractogram comprising, among other peaks, characteristic peaks, expressed in degrees 2θ (±0.2°), at 7.5°, 10.9° and 12.6°. Preferably, the PXRD diffractogram further comprises at least three peaks, expressed in degrees 2θ (±0.2°), selected from the group consisting of 13.9°, 14.8°, 17.2°, 18.1°, 19.4°, 20.8°, 21.7°, 22.6° and 24.3°. More preferably, the PXRD diffractogram further comprises peaks, expressed in degrees 2θ (±0.2°), at 13.9°, 14.8°, 17.2°, 18.1°, 19.4°, 20.8°, 21.7°, 22.6° and 24.3°.

Figure 4:
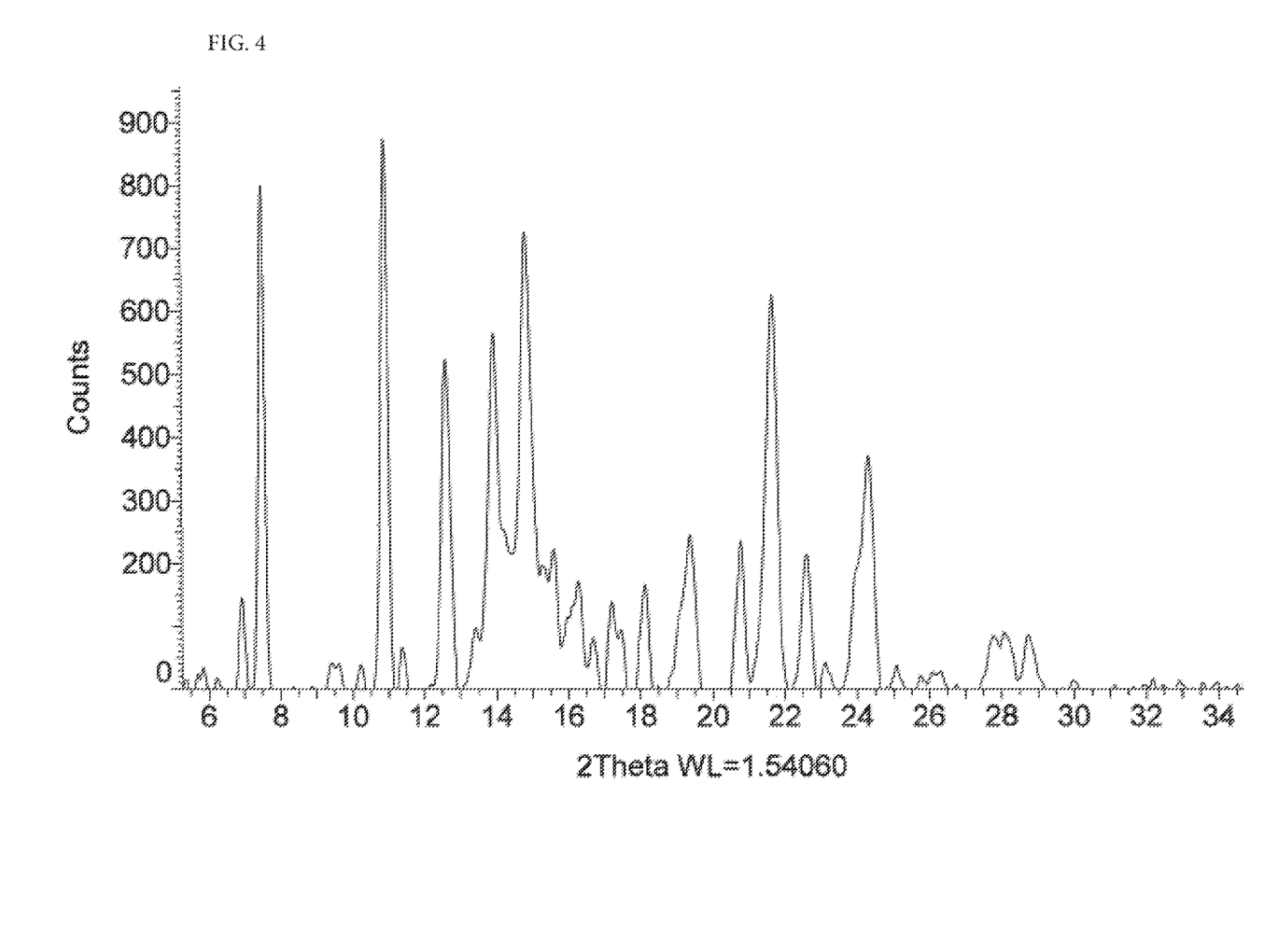
FIG. 4 is a representative PXRD diffractogram of Acalabrutinib Form APO-IV as prepared in Example 5.

An illustrative PXRD diffractogram of Acalabrutinib Form APO-IV, as prepared in Example 4, is shown in FIG. 4. A peak listing, comprising peaks from the PXRD diffractogram in FIG. 4, and their relative intensities, is provided in Table 4. Although illustrative of the PXRD diffractogram that is provided for the Acalabrutinib Form APO-IV of the present invention, the relative intensities of the peaks are variable. Thus, depending on a particular sample, the prominence or relative intensity of the peaks observed may differ from those in the illustrative PXRD diffractogram and peak listing.

TABLE 4

Relative peak intensities of
Acalabrutinib Form APO-IV from FIG. 4

| Angle (°2θ) | Relative intensity (%) |
|---|---|
| 6.95 | 16.5 |
| 7.49 | 91.7 |
| 10.90 | 100.0 |
| 12.62 | 59.5 |
| 13.93 | 64.6 |
| 14.82 | 83.0 |
| 15.58 | 25.5 |
| 17.20 | 15.9 |
| 18.12 | 19.0 |
| 19.36 | 28.0 |
| 20.78 | 27.1 |
| 21.66 | 71.6 |
| 22.60 | 24.4 |
| 24.32 | 42.4 |

As described in Example 5, Acalabrutinib Form APO-IV can be prepared by combining Acalabrutinib and chlorobenzene and heating the mixture, preferably to approximately 60° C. or until dissolution has been achieved, followed by a period of cooling. Filtration of the resulting suspension provides Acalabrutinib Form APO-IV having a PXRD diffractogram consistent with FIG. 4.

In a fifth embodiment of the present invention, there is provided a new crystalline form of Acalabrutinib, Acalabrutinib Form APO-V, which is a co-crystal of Acalabrutinib and urea. Preferably, in Acalabrutinib Form APO-V, the molar ratio of Acalabrutinib to urea is approximately 1:2.

Acalabrutinib Form APO-V can be characterized by a PXRD diffractogram comprising, among other peaks, characteristic peaks, expressed in degrees 2θ (±0.2°), at 5.4°, 6.6° and 11.0°. Preferably, the PXRD diffractogram further comprises at least three peaks, expressed in degrees 2θ (±0.2°), selected from the group consisting of 10.1°, 13.2°, 15.1°, 17.3°, 19.9°, 21.1° and 22.2°. More preferably, the PXRD diffractogram further comprises peaks, expressed in degrees 2θ (±0.2°), at 10.1°, 13.2°, 15.1°, 17.3°, 19.9°, 21.1° and 22.2°. PXRD studies of capped and uncapped samples of Acalabrutinib Form APO-V have shown that this crystalline form is stable following storage in stability chambers maintained at 40° C./75% RH for at least 14 days.

Figure 5:
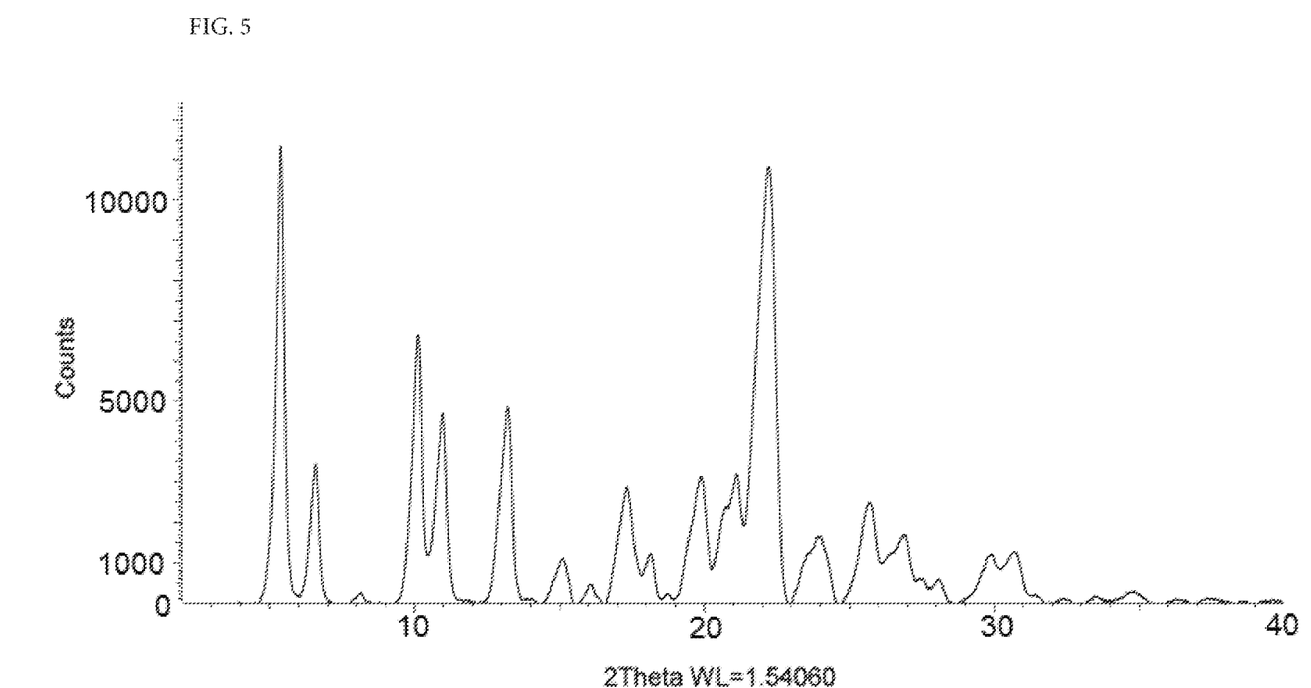
FIG. 5 is a representative PXRD diffractogram of Acalabrutinib Form APO-V as prepared in Example 6.

An illustrative PXRD diffractogram of Acalabrutinib Form APO-V, as prepared in Example 6, is shown in FIG. 5. A peak listing, comprising representative peaks from the PXRD diffractogram in FIG. 5, and their relative intensities, is provided in Table 5. Although illustrative of the PXRD diffractogram that is provided for the Acalabrutinib Form APO-V of the present invention, the relative intensities of the peaks are variable. Thus, depending on a particular sample, the prominence or relative intensity of the peaks observed may differ from those in the illustrative PXRD diffractogram and peak listing.

TABLE 5

Relative peak intensities of
Acalabrutinib Form APO-V from FIG. 5

| Angle (°2θ) | Relative intensity (%) |
|---|---|
| 5.38 | 100.0 |
| 6.59 | 30.3 |
| 8.11 | 2.0 |
| 10.12 | 58.7 |
| 10.98 | 41.6 |
| 13.22 | 42.9 |
| 15.12 | 9.6 |
| 16.11 | 4.0 |
| 17.33 | 25.3 |
| 19.90 | 27.5 |
| 21.10 | 28.0 |

TABLE 5-continued

Relative peak intensities of
Acalabrutinib Form APO-V from FIG. 5

| Angle (°2θ) | Relative intensity (%) |
|---|---|
| 22.22 | 95.6 |
| 24.01 | 14.6 |
| 25.70 | 22.0 |

A described in Example 6, Acalabrutinib Form APO-V can be prepared by combining urea and Acalabrutinib in a solvent, preferably ethanol, and maintaining the mixture at a suitable temperature, preferably in the range of room temperature to 60° C., followed by a period of cooling, if necessary. Alternatively, a mixture of ethanol and methanol can be used as the solvent, preferably having a volume ratio of ethanol:methanol of from approximately 8:2 to 9:1. The molar ratio of Acalabrutinib to urea is at least approximately 1:2, and is more preferably 1:4. Filtration of the resulting suspension provides Acalabrutinib Form APO-V having a PXRD diffractogram consistent with FIG. 5.

Acalabrutinib Form APO-V can be further characterized based on the amount of water present. Preferably, in Acalabrutinib Form APO-V, the weight percentage of water is between approximately 2.0 wt % and approximately 4.0 wt %, and is most preferably approximately 3.0 wt %.

In a further embodiment of the invention, there is provided a pharmaceutical composition of a crystalline form of Acalabrutinib comprising co-crystallized Acalabrutinib and a co-former selected from the group consisting of urea, nicotinamide and L-sorbitol, with one or more pharmaceutically acceptable excipients. Preferably, the pharmaceutical composition is a solid dosage form suitable for oral administration, such as a capsule, tablet, pill, powder or granulate. Most preferably, the pharmaceutical composition is a capsule. Preferably, the pharmaceutical composition provides a dose of Acalabrutinib that is equivalent to the 100 mg of Acalabrutinib found in CALQUENCE® drug products.

Suitable pharmaceutically acceptable excipients are preferably inert with respect to the crystalline form of Acalabrutinib of the present invention, and may include, for example, one or more excipients selected from binders such as lactose, starches, modified starches, sugars, gum acacia, gum tragacanth, guar gum, pectin, wax binders, microcrystalline cellulose, methylcellulose, carboxymethylcellulose, hydroxypropyl methylcellulose, hydroxyethyl cellulose, hydroxypropyl cellulose, copolyvidone, gelatine, polyvinylpyrollidone (PVP) and sodium alginate; fillers or diluents such as lactose, sugar, starches, modified starches, mannitol, sorbitol, inorganic salts, cellulose derivatives (e.g., microcrystalline cellulose, cellulose), calcium sulphate, xylitol and lactitol; disintegrants such as croscarmellose sodium, crospovidone, polyvinylpyrrolidone, sodium starch glycollate, corn starch, microcrystalline cellulose, hydroxypropyl methylcellulose and hydroxypropyl cellulose; lubricants such as magnesium stearate, magnesium lauryl stearate, sodium stearyl fumarate, stearic acid, calcium stearate, zinc stearate, potassium benzoate, sodium benzoate, myristic acid, palmitic acid, mineral oil, hydrogenated castor oil, medium-chain triglycerides, poloxamer, polyethylene glycol and talc; and dispersants or solubility enhancing agents, such cyclodextrins, glyceryl monostearate, hypromellose, meglumine, Poloxamer, polyoxyethylene castor oil derivatives, polyoxyethylene stearates, polyoxylglycerides, povidone, and stearic acid. Other excipients including preservatives, stabilisers, anti-oxidants, silica flow conditioners, antiadherents or glidants may be added as required. Other suitable excipients and the preparation of solid oral dosage forms is well known to person of skill in the art, and is described generally, for example, in Remington The Science and Practice of Pharmacy 21$^{st}$ Edition (Lippincott Williams & Wilkins: Philadelphia; 2006; Chapter 45).

Optionally, when the pharmaceutical compositions are solid dosage forms, the solid dosage forms may be prepared with coatings, such as enteric coatings and extended release coatings, using standard pharmaceutical coatings. Such coatings, and their application, are well known to persons skilled in the art, and are described, for example, in Remington The Science and Practice of Pharmacy 21$^{st}$ Edition (Lippincott Williams & Wilkins: Philadelphia; 2006; Chapter 46).

EXAMPLES

The following non-limiting examples are illustrative of some of the aspects and embodiments of the invention described herein.

The Acalabrutinib used as a starting material in the following examples was consistent with amorphous Acalabrutinib, which is reported in WO 2017/002095 A1. Other polymorphic forms are equally suitable as starting material, provided dissolution of the other form occurs when preparing the novel crystalline forms of Acalabrutinib of the present invention.

PXRD Analysis:

PXRD diffractograms were recorded on a Bruker D8 Discover powder X-ray diffractometer (Bruker-AXS, Karlsruhe, Germany). The sample holder was oscillated along X and Y axes during the measurement. The generator was a Micro-focus X-ray source (IMSTube: Cu tube with 1.54184 A) with a voltage of 50 kV and current of 1.00 mA, using a divergence slit of 0.3 mm and collimator of 0.3 mm. For each sample, one frame was collected using a still scan with a Pilatus 3R-100 kA detector at the distance of 154.72 mm from the sample. Raw data were evaluated using the program EVA (Bruker-AXS, Karlsruhe, Germany).

Example 1

Preparation of Acalabrutinib Form APO-I

To a solution of Acalabrutinib (500 mg, 1.07 mmol) in methanol (2.5 mL) was added urea (258 mg, 4.29 mmol), and the resulting cloudy solution was heated to 55° C. for 2 hours, providing a clear solution. The temperature of the heating bath was then lowered to 40° C., and the mixture was stirred for 2 hours over which time turbidity developed. The turbid mixture was cooled to room temperature and stirred overnight to afford a suspension. Following addition of methanol (0.6 mL), the solid was collected by filtration and washed with methanol (0.5 mL) to afford Acalabrutinib Form APO-I (260 mg) as a greenish solid. $^1$H NMR analysis of the solid (d$_6$-DMSO)) identified a molar ratio of Acalabrutinib:urea of approximately 1:2.6.

Example 2

Preparation of Acalabrutinib Form APO-I

To a solution of Acalabrutinib (50 mg, 0.11 mmol) in methanol (0.5 mL) was added urea (19.35 mg, 0.32 mmol), and the resulting cloudy solution was heated to 55° C. for 1.5 hours. The temperature of the heating bath was then lowered to 40° C. and the mixture was stirred for 1 hour further prior to cooling to room temperature and stirring overnight. The resulting solution was treated with acetonitrile (0.2 mL) followed by urea (6.5 mg, 0.11 mmol), and then cooled to 0° C. overnight to facilitate crystallization. Following this time, the solution was seeded with Acalabrutinib Form APO-I (1 mg) prepared by the method of Example 1, and the solution was maintained at 0° C. for 2 days. The resulting solid was collected by filtration and dried in vacuo at room temperature for several hours to afford Acalabrutinib Form APO-I (13.4 mg). $^1$H NMR analysis of the solid (d$_6$-DMSO)) showed a molar ratio of Acalabrutinib:urea of approximately 1:2.2. The purity of the starting material Acalabrutinib by HPLC was 96.3% a/a, while the purity of the isolated Acalabrutinib Form APO-I by HPLC was 98.1% a/a. The PXRD diffractogram of a sample prepared by this method is shown in FIG. 1.

$^1$H-NMR (d$_6$-DMSO, 300 MHz; substance is comprised of rotamers) δ: 1.62 and 2.01 (3H, s (combined peaks)), 2.08-2.17 (1H, m), 2.18-2.42 (2H, m), 3.31 (1H, s), 3.51-3.69 (1H, m), 3.82 (1H, t, J=6.5 Hz), 5.41 (br s, 10.3H, urea signal) 5.45-5.32 and 5.67-5.77 (1H, each m), 6.14 and 6.20 (2H, each s), 7.14 (1H, dd, J=4.9 Hz, 11.8 Hz), 7.18 (1H, ddd, J=0.9 Hz, 4.9 Hz, 7.32 Hz), 7.77-7.90 (4H, m), 8.16 (2H, dd, J=1.9 Hz, 8.37 Hz), 8.22 (1H, d, J=8.4 Hz), 8.41 (1H, m), 10.85 (1H, s).

Example 3

Preparation of Acalabrutinib Form APO-II

A mixture of Acalabrutinib (3 mg, 0.006 mmol) and nicotinamide (3 mg, 0.024 mmol) in acetone (30 μL) was subjected to three cycles of the following temperature regime: heat from 20° C. to 50° C.; hold at 50° C. for 1 hour; and cool from 50° C. to 20° C. in 10° C. intervals with a hold period of 1 hour at each interval (i.e., 40° C., 30° C., 20° C.). The solid was collected by decantation to afford Acalabrutinib Form APO-II. $^1$H NMR analysis of the solid (d$_6$-DMSO)) showed a molar ratio of Acalabrutinib:nicotinamide of approximately 1:2. The PXRD diffractogram of a sample prepared by this method is shown in FIG. 2.

Example 4

Preparation of Acalabrutinib Form APO-III

A mixture of Acalabrutinib (3 mg, 0.006 mmol) and L-sorbitol (3 mg, 0.024 mmol) in acetone (30 μL) was subjected to three cycles of the following temperature regime: heat from 20° C. to 50° C.; hold at 50° C. for 1 hour; and cool from 50° C. to 20° C. in 10° C. intervals with a hold period of 1 hour at each interval (i.e., 40° C., 30° C., 20° C.). The solid was collected by decantation to afford Acalabrutinib Form APO-III. $^1$H NMR analysis of the solid (d$_6$-DMSO)) showed a molar ratio of Acalabrutinib:L-sorbitol of approximately 1:1. The PXRD diffractogram of a sample prepared by this method is shown in FIG. 3.

Example 5

Preparation of Acalabrutinib Form APO-IV

A suspension of Acalabrutinib (130 mg, 0.28 mmol) in chlorobenzene (2.4 mL) was heated to 50° C. for 1 hour to afford a clear solution. The solution was cooled to 25° C., whereupon crystallization occurred. The solid was collected by filtration, washed with a minimal quantity of heptane, and dried in vacuo at room temperature for 16 hours to afford Acalabrutinib Form APO-IV (60 mg) as a light purple solid. The PXRD diffractogram of a sample prepared by this method is shown in FIG. 4.

Example 6

Preparation of Acalabrutinib Form APO-V

A suspension of Acalabrutinib (2.0 g, 4.3 mmol) and urea (1.0 g, 17.2 mmol) in ethanol (20 mL) was heated to approximately 55° C. for 30 minutes to afford a cloudy solution. The solution was cooled to approximately 45° C. and stirred for 2 hours over which time a suspension developed, and then cooled to room temperature and stirred for a further 2 hours. The mixture was further cooled to 0-5° C. and stirred for 1.5 hours. The resulting solid was collected by filtration, washed with ethanol (3 mL), and dried in vacuo at 35° C. for 2 hours to afford Acalabrutinib Form APO-V (1.8 g) as a greenish solid. The PXRD diffractogram of a sample prepared by this method is shown in FIG. 5. $^1$H NMR analysis of the solid (d$_6$-DMSO)) showed a molar ratio of Acalabrutinib:urea of approximately 1:1.7. The water content (Karl Fischer) of the sample was 2.9 wt %.

What is claimed is:

1. A crystalline form of Acalabrutinib that is a co-crystal of Acalabrutinib and urea, wherein the molar ratio of Acalabrutinib to urea is between approximately 1:1.5 and approximately 1:2.5.

2. The co-crystal of claim 1, wherein the molar ratio of Acalabrutinib to urea is approximately 1:2.

3. The co-crystal of claim 1, characterized by a PXRD diffractogram comprising peaks, expressed in degrees 2θ (±0.2°), at 5.4°, 7.3° and 10.0°.

4. The co-crystal of claim 3, further comprising at least three peaks, expressed in degrees 2θ (±0.2°), selected from the group consisting of: 10.4°, 11.4°, 11.8°, 12.8°, 15.3°, 17.0°, 18.4°, 20.1°, 20.8° and 21.3°.

5. The co-crystal of claim 3, further comprising peaks, expressed in degrees 2θ (±0.2°), at 10.4°, 11.4°, 11.8°, 12.8°, 15.3°, 17.0°, 18.4°, 20.1°, 20.8° and 21.3°.

6. The co-crystal of claim 1 characterized by a PXRD diffractogram comprising peaks, expressed in degrees 2θ (±0.2°), at 5.4°, 6.6° and 11.0°.

7. The co-crystal of claim 6, further comprising at least three peaks, expressed in degrees 2θ (±0.2°), selected from the group consisting of: 10.1°, 13.2°, 15.1°, 17.3°, 19.9°, 21.1° and 22.2°.

8. The co-crystal of claim 6, further comprising peaks, expressed in degrees 2θ (±0.2°), at 10.1°, 13.2°, 15.1°, 17.3°, 19.9°, 21.1° and 22.2°.

9. A pharmaceutical composition comprising the crystalline form of Acalabrutinib according to claim 1, and one or more pharmaceutically acceptable excipients.

* * * * *